(12) United States Patent  
Ishihara

(10) Patent No.: US 10,086,268 B2  
(45) Date of Patent: Oct. 2, 2018

(54) EYEBALL MOVEMENT DETECTION DEVICE

(71) Applicant: SHARP KABUSHIKI KAISHA, Sakai, Osaka (JP)

(72) Inventor: Takehisa Ishihara, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 27 days.

(21) Appl. No.: 15/520,624

(22) PCT Filed: Aug. 26, 2015

(86) PCT No.: PCT/JP2015/074115  
§ 371 (c)(1),  
(2) Date: Apr. 20, 2017

(87) PCT Pub. No.: WO2016/080042  
PCT Pub. Date: May 26, 2016

(65) Prior Publication Data  
US 2017/0312622 A1   Nov. 2, 2017

(30) Foreign Application Priority Data

Nov. 19, 2014 (JP) ................................ 2014-234970

(51) Int. Cl.  
*A63F 13/213* (2014.01)  
*A61B 3/113* (2006.01)  
(Continued)

(52) U.S. Cl.  
CPC ............ *A63F 13/213* (2014.09); *A61B 3/113* (2013.01); *A61B 5/0075* (2013.01); *A61B 5/01* (2013.01);  
(Continued)

(58) Field of Classification Search  
CPC ........... A63F 13/213; A63F 2300/1087; A63B 3/113; G06F 3/013  
See application file for complete search history.

(56) References Cited

U.S. PATENT DOCUMENTS 5,367,315 A * 11/1994 Pan .................... G06F 3/013  
345/156  
5,402,109 A * 3/1995 Mannik ............... G02C 5/001  
340/575  
5,508,759 A * 4/1996 Konishi .............. A61B 3/113  
351/205

(Continued)

FOREIGN PATENT DOCUMENTS

CN           1367662 A       9/2002  
JP       2013-244370 A      12/2013  
(Continued)

*Primary Examiner* — Steven J Hylinski  
(74) *Attorney, Agent, or Firm* — Birch, Stewart, Kolasch & Birch, LLP

(57) ABSTRACT

An eyeball movement detection device (1) detects an eyeball movement of an eye in a side-to-side direction on the basis of a time shift in difference between an output from a far-infrared sensor (11) having directivity to an edge of an exposed surface of an eyeball on the side of the inner corner of the eye and an output from a far-infrared sensor (12) having directivity to an edge of the exposed surface of the eyeball on the side of the outer corner of the eye. This makes it possible to detect an eyeball movement in a noncontact manner, with a light weight, and with low power consumption.

5 Claims, 12 Drawing Sheets

| 11:FAR-INFRARED SENSOR | 20:CONTROL SECTION |
|---|---|
| 12:FAR-INFRARED SENSOR | 30:SPECTACLES |
| 13:FAR-INFRARED SENSOR | 31:FRAME |
| 14:FAR-INFRARED SENSOR | |

| 40:RIGHT EYE | 51:EDGE |
|---|---|
| 41:INNER CORNER OF EYE | 52:EDGE |
| 42:OUTER CORNER OF EYE | 53:EDGE |
| 43:UPPER EYELID | 54:EDGE |
| 44:LOWER EYELID | 61:TRANSVERSE AXIS |
| 50:EXPOSED SURFACE OF EYEBALL | 62:LONGITUDINAL AXIS |

(51) Int. Cl.
*G06F 3/00* (2006.01)
*A63F 13/65* (2014.01)
*A61B 5/00* (2006.01)
*A61B 5/01* (2006.01)
*A61B 5/11* (2006.01)
*G06F 3/01* (2006.01)

(52) U.S. Cl.
CPC .......... *A61B 5/1128* (2013.01); *A61B 5/6803* (2013.01); *A63F 13/65* (2014.09); *A63F 2300/1087* (2013.01); *G06F 3/013* (2013.01)

(56) References Cited

U.S. PATENT DOCUMENTS

| | | | | |
|---|---|---|---|---|
| 5,530,495 A * | 6/1996 | Lamprecht | ............. | A61B 3/113 351/205 |
| 5,552,854 A * | 9/1996 | Nishimura | ............. | A61B 3/113 351/210 |
| 5,583,795 A * | 12/1996 | Smyth | ................. | A61B 3/0025 359/630 |
| 5,592,401 A * | 1/1997 | Kramer | ............. | A63B 69/3608 340/524 |
| 5,966,197 A * | 10/1999 | Yee | ......................... | A61F 9/008 351/210 |
| 6,163,281 A * | 12/2000 | Torch | ................... | A61B 3/0066 340/575 |
| 6,283,954 B1 | 9/2001 | Yee | | |
| 6,322,216 B1 * | 11/2001 | Yee | ......................... | A61B 3/113 351/210 |
| 6,604,825 B2 * | 8/2003 | Lai | ......................... | A61B 3/113 351/210 |
| 7,164,117 B2 * | 1/2007 | Breed | ............... | B60R 21/01516 250/208.1 |
| 8,820,782 B2 * | 9/2014 | Breed | ..................... | B60J 10/00 280/735 |
| 2010/0295769 A1 * | 11/2010 | Lundstrom | ............. | G06F 3/011 345/156 |
| 2012/0021806 A1 * | 1/2012 | Maltz | ...................... | H04W 4/20 455/566 |
| 2012/0177266 A1 | 7/2012 | Tsukizawa et al. | | |
| 2013/0324881 A1 | 12/2013 | Kanoh et al. | | |
| 2014/0160433 A1 * | 6/2014 | Brown, Jr. | ............. | A61B 3/113 351/209 |
| 2014/0160434 A1 * | 6/2014 | Brown, Jr. | ............. | A61B 3/113 351/210 |

FOREIGN PATENT DOCUMENTS

JP 5529660 B2 6/2014
KR 20150072778 A * 6/2015

* cited by examiner

| 40:RIGHT EYE | 51:EDGE |
|---|---|
| 41:INNER CORNER OF EYE | 52:EDGE |
| 42:OUTER CORNER OF EYE | 53:EDGE |
| 43:UPPER EYELID | 54:EDGE |
| 44:LOWER EYELID | 61:TRANSVERSE AXIS |
| 50:EXPOSED SURFACE OF EYEBALL | 62:LONGITUDINAL AXIS |

SIDE OF OUTER CORNER OF EYE

SIDE OF INNER CORNER OF EYE

40: RIGHT EYE
41: INNER CORNER OF EYE
42: OUTER CORNER OF EYE
50: EXPOSED SURFACE OF EYEBALL
51: EDGE
52: EDGE
55: EXPOSED PART FROM ORBIT

40: RIGHT EYE
43: UPPER EYELID
44: LOWER EYELID
50: EXPOSED SURFACE OF EYEBALL
53: EDGE
54: EDGE
56: EXPOSED PART FROM ORBIT

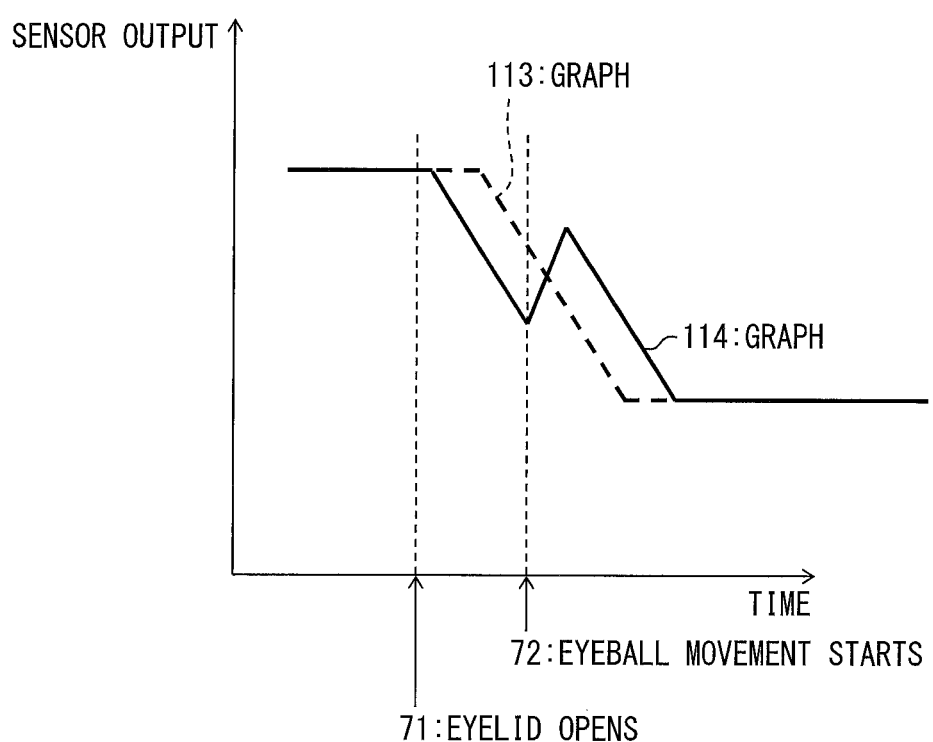

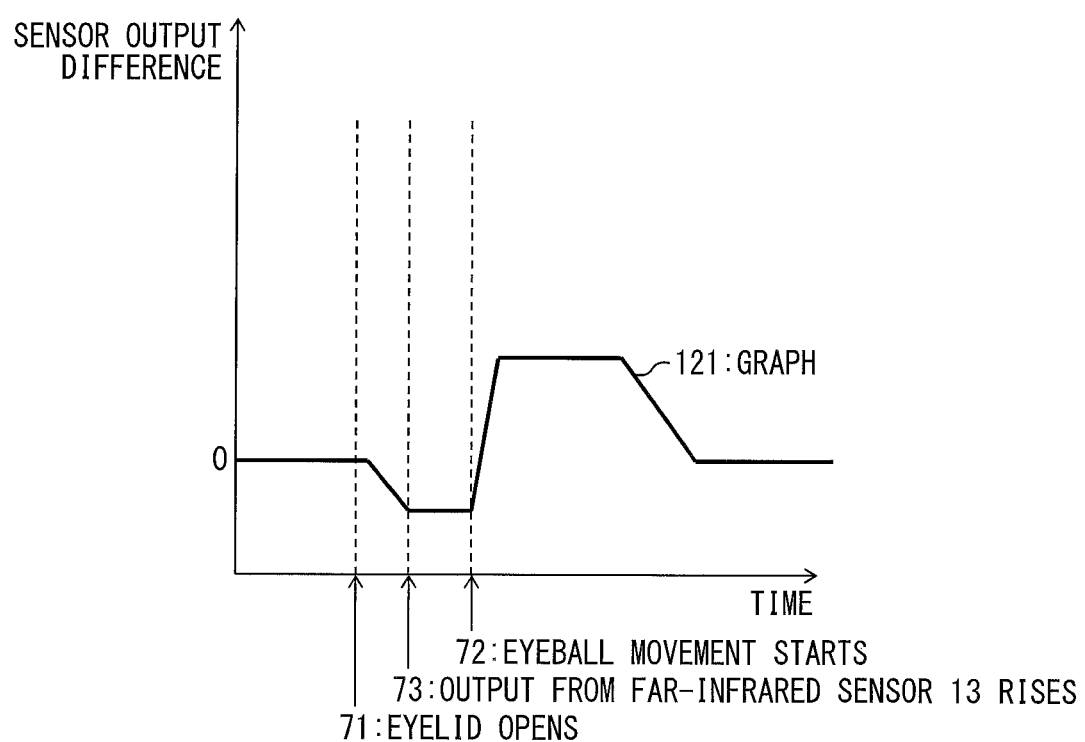

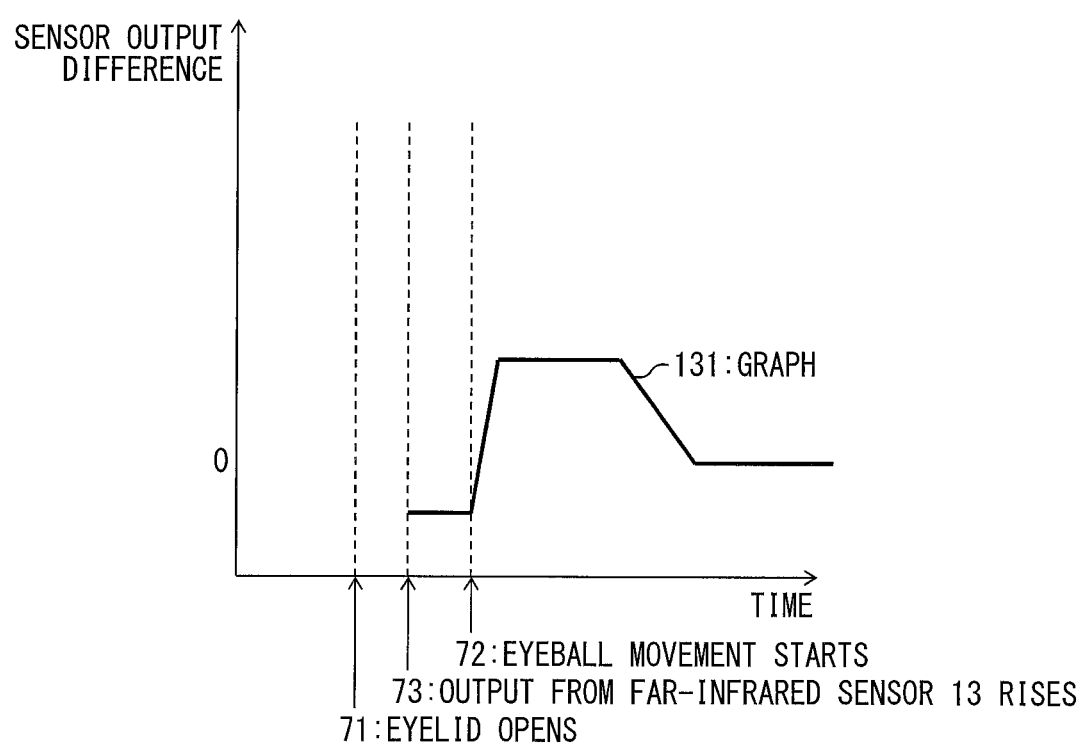

EYEBALL MOVEMENT DETECTION DEVICE

TECHNICAL FIELD

The present invention relates to a technology for detecting an eyeball movement.

BACKGROUND ART

The popularization of devices, such as head mount display devices and spectacle display devices, that can present pictures right in front of a user's eyes has recently been exploding. Along with this popularization, various devices that use results of detection of eye movements, as well as devices that are used with hands, such as mouses and joysticks, have been proposed and sold as devices for operating computers.

There have conventionally been proposed various methods for detecting an eye movement. Typical examples of these methods are the EOG method, the sclera reflection method, the cornea reflection method, and the search coil method. In the EOG method, the presence in a corneal section of a positive potential that is higher by 10 to 30 μV than that in a retinal portion is detected by electrodes placed around an eye. In the sclera reflection method, a pupillary movement is detected by a visible camera on the basis of a difference in reflectivity between the iris and pupil of an eye and the white of the eye. In the cornea reflection method, an eye is irradiated with low-intensity infrared radiation, and a reflection of the infrared radiation by the cornea is detected by an infrared camera. In the search coil method, the position of a contact lens around which a coil is wound is detected.

However, these methods have the following shortcomings. The EOG method causes the user the inconvenience of the electrodes sticking to the skin, and the electrodes are vulnerable to electromagnetic noise, sweat, and sebum. The sclera reflection method requires image processing and therefore entails increases in power consumption and weight of a device that employs this method. The cornea reflection method requires irradiation of the eye with light and image processing and therefore entails increases in power consumption and weight of a device that employs this method. The search coil method causes the user the inconvenience of wearing contact lenses.

Various technologies for alleviating the shortcomings of the EOG method have conventionally been proposed. One of the technologies is eyewear disclosed in PTL 1. This eyewear includes a frame, a pair of nose pads, and first and second electrodes provided on the respective surfaces of the pair of nose pads to detect an eye potential.

CITATION LIST

Patent Literature

PTL 1: Japanese Unexamined Patent Application Publication No. 2013-244370 (published on Dec. 9, 2013)

SUMMARY OF INVENTION

Technical Problem

In order to detect an eyeball movement with the eyewear of PTL 1, it is necessary to bring the first and second electrodes into contact with the user's skin. As such, this eyewear still has the shortcomings of causing the user the inconvenience of the first and second electrodes sticking to the skin and being vulnerable to electromagnetic noise, sweat, and sebum.

The present invention is one made to solve the foregoing problems. It is an object of the present invention to propose an eyeball movement detection device that can detect an eyeball movement in a noncontact manner, with a light weight, and with low power consumption.

Solution to Problem

In order to solve the foregoing problems, an eyeball movement detection device includes:

a first far-infrared sensor having directivity to a first edge of an exposed surface of an eyeball of an eye of a user;

a second far-infrared sensor having directivity to a second edge of the exposed surface of the eyeball, the second edge being opposed to the first edge;

a first output difference calculation section that calculates a difference between an output from the first far-infrared sensor and an output from the second far-infrared sensor; and a detection section that detects an eyeball movement of the eyeball on the basis of a time shift in the difference thus calculated.

Advantageous Effects of Invention

An aspect of the present invention brings about an effect of making it possible to detect an eyeball movement in a noncontact manner, with a light weight, and with low power consumption.

BRIEF DESCRIPTION OF DRAWINGS

FIG. 10 is a diagram showing an example of a time shift in output from a far-infrared sensor with directivity to an edge on the side of the upper eyelid and an example of a time shift in output from a far-infrared sensor with directivity to an edge on the side of the lower eyelid as observed when the upper eyelid of the right eye opened and then the user made an eyeball movement in which he/she transferred his/her line of sight upward in Embodiment 2 of the present invention.

FIG. 11 is a diagram showing an example of a time shift in difference between the output from the far-infrared sensor with directivity to the edge on the side of the upper eyelid and the output from the far-infrared sensor with directivity to the edge on the side of the lower eyelid as observed when the upper eyelid of the right eye opened and then the user made an eyeball movement in which he/she transferred his/her line of sight upward in Embodiment 2 of the present invention.

FIG. 12 is a diagram showing an example of a time shift in difference between the output from the far-infrared sensor with directivity to the edge on the side of the upper eyelid of the right eye and the output from the far-infrared sensor with directivity to the edge on the side of the lower eyelid of the right eye as observed after detection of a time difference between a rising edge of the output from the far-infrared sensor with directivity to the edge on the side of the upper eyelid and a rising edge of the output from the far-infrared sensor with directivity to the edge on the side of the lower eyelid in Embodiment 2 of the present invention.

DESCRIPTION OF EMBODIMENTS

Embodiment 1

A first embodiment according to the present invention is described below with reference to FIGS. 1 to 8.

(Eyeball Movement Detection Device 1)

Figure 1:
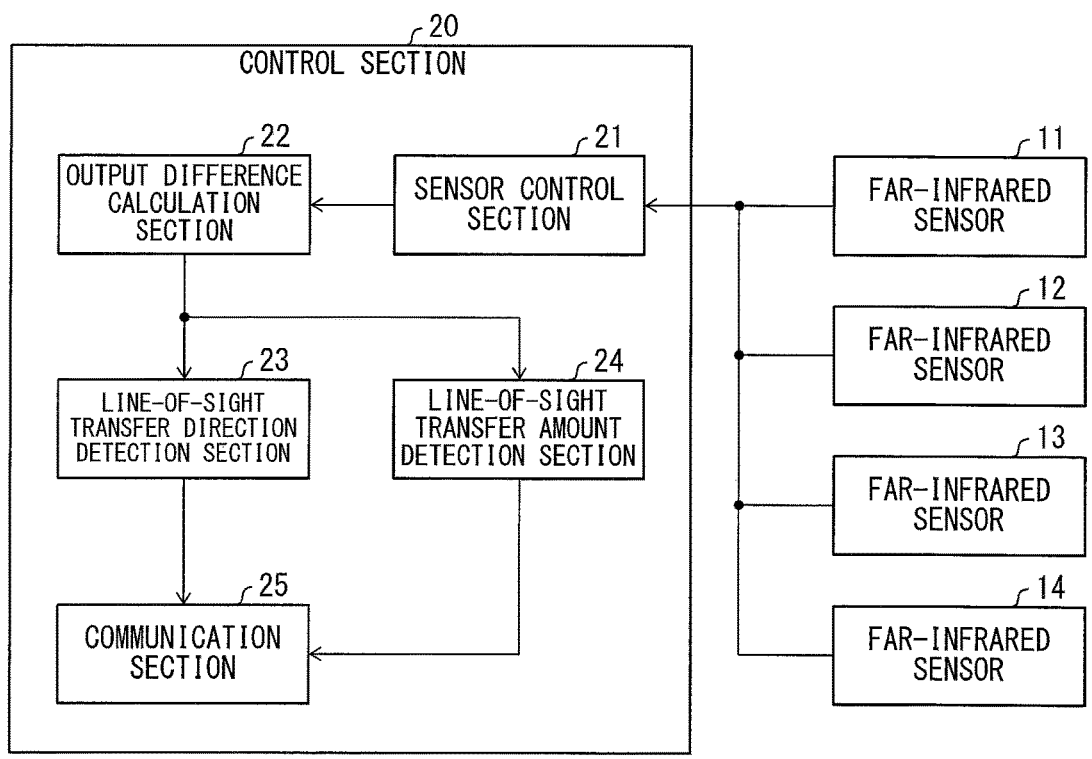
FIG. 1 is a block diagram showing the main components of an eyeball movement detection device according to Embodiment 1 of the present invention.

FIG. 1 is a block diagram showing the main components of an eyeball movement detection device 1 according to the present embodiment. As shown in FIG. 1, the eyeball movement detection device 1 includes a far-infrared sensor 11 (first far-infrared sensor), a far-infrared sensor 12 (second far-infrared sensor), a far-infrared sensor 13 (first far-infrared sensor, third far-infrared sensor), a far-infrared sensor 14 (second far-infrared sensor, fourth far-infrared sensor), and a control section 20.

Each of the far-infrared sensors 11 to 14 is a sensor that receives far-infrared radiation and outputs a signal corresponding to the intensity of the far-infrared radiation. In the present embodiment, the far-infrared sensors 11 to 14 are used for measuring the temperature of an exposed surface of an eyeball. An eyeball emits far-infrared radiation with a peak wavelength of approximately 9 µm when it has a temperature that is close to body temperature. Examples of the far-infrared sensors 11 to 14 that are used for detecting such a temperature are photodiodes, thermopiles, or bolometers that are made of a compound such as InSb.

The control section 20 is a member that exercises integrated control of how the eyeball movement detection device 1 operates. As shown in FIG. 1, the control section 20 includes a sensor control section 21, an output difference calculation section 22, a line-of-sight transfer direction detection section 23 (detection section, first detection section, second detection section), a line-of-sight transfer amount detection section 24 (detection section, first detection section, second detection section), and a communication section 25. As will be described in detail later, the control section 20 calculates differences in output among the far-infrared sensors 11 to 14 and detects an eyeball movement on the basis of a time shift in the differences.

(Spectacles 30)

Figure 2:
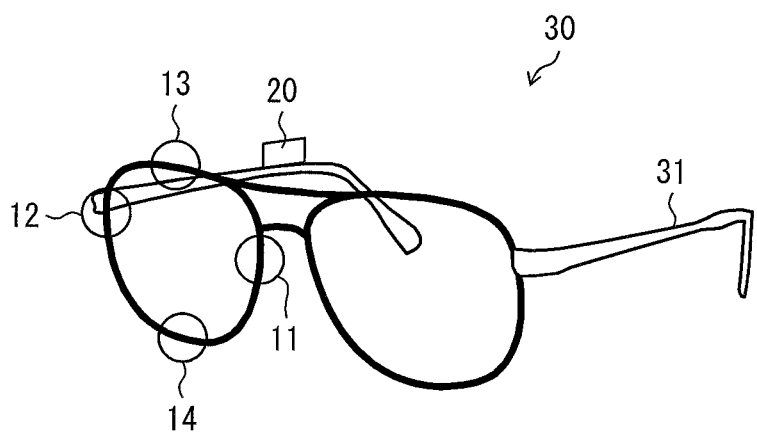
FIG. 2 is a diagram showing the main components of spectacles according to Embodiment 1 of the present invention.

The eyeball movement detection device 1 according to the present embodiment is incorporated into spectacles 30, and when a user is wearing the spectacles 30, the eyeball movement detection device 1 detects an eyeball movement of the user. FIG. 2 is a diagram showing the main components of the spectacles 30 according to the present embodiment. As shown in FIG. 2, the spectacles 30 include a frame 31 and the eyeball movement detection device 1 incorporated into the frame 31. The far-infrared sensors 11 to 14 are incorporated into the right rim of the frame 31 (i.e. the outside edge of the frame 31 that surrounds the right lens). Meanwhile, the control section 20 is incorporated into the right temple of the frame 31 (i.e. the part of the frame 31 that passes over the right ear).

The far-infrared sensors 11 to 14 take the form of very small sensors and can therefore be incorporated into the frame 31 without problems. For example, when the far-infrared sensors 11 to 14 are Texas Instruments' TMP006 infrared thermopiles, the far-infrared sensors 11 to 14 may be 1.6 mm×1.6 mm in size. It should be noted that in a case where the far-infrared sensors 11 to 14 are TMP006 infrared thermopiles, the TMP006 infrared thermopiles may be combined with silicon diffractive lenses, which are flat-plate lenses, to have narrower viewing angles, as the TMP006 infrared thermopiles have wide viewing angles. It should also be noted that these lenses may be replaced by aperture diaphragms. This makes it possible to limit the fields of view of the far-infrared sensors 11 to 14 so that the far-infrared sensors 11 to 14 have directivity to particular edges of an exposed surface 50 of an eyeball.

In the present embodiment, the spectacles 30 are configured such that the far-infrared sensors 11 to 14 are connected to the control section 20 through wires (not illustrated) and all outputs (signals) from the far-infrared sensors 11 to 14 are sent to the control section 20. Further, the control section 20 is communicably connected to an external computer (not illustrated), and all results of detection of eyeball movements by the control section 20 are sent to the external computer. The external computer executes a process according to a result of detection of an eyeball movement as received from the control section 20. This allows the user wearing the spectacles 30 to operate the external computer with an eye movement without using his/her hands.

The connection between the control section 20 and the external computer may be either wired or wireless. In the case of wired connection, the control section 20 is connected to the external computer through a predetermined flexible substrate or wire.

(Directivity of Far-Infrared Sensors 11 to 14)

Figure 3:
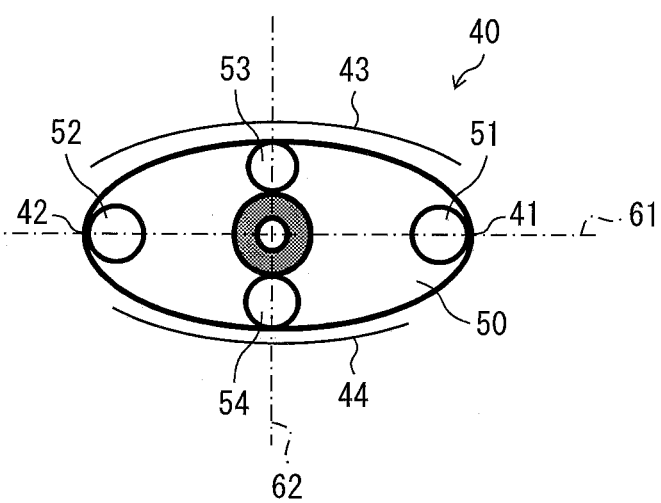
FIG. 3 is a diagram describing the right eye of a user wearing the spectacles according to Embodiment 1 of the present invention.

FIG. 3 is a diagram describing the right eye 40 of the user wearing the spectacles 30. In FIG. 3, the user directs his/her line of sight (eye line) right to the front perpendicular to the surface of paper. The far-infrared sensors 11 to 14 have directivity to any particular edges of the exposed surface 50 of the eyeball that correspond to the positions in the spectacles 30 where the respective sensors are installed. In other words, the far-infrared sensors 11 to 14 do not have fields of view all over the exposed surface 50 of the eyeball but have fields of view only at the corresponding edges.

Specifically, the far-infrared sensor 11 has directivity to an edge 51 (first edge) of the exposed surface 50 of the eyeball on the side of the inner corner 41 of the eye. Further, the far-infrared sensor 12 has directivity to an edge 52 (second edge) of the exposed surface 50 of the eyeball on the side of the outer corner 42 of the eye. Further, the far-infrared sensor 13 has directivity to an edge 53 (first edge, third edge) of the exposed surface 50 of the eyeball on the side of the upper eyelid 43. Further, the far-infrared sensor 14 has directivity to an edge 54 (second edge, fourth edge) of the exposed surface 50 of the eyeball on the side of the lower eyelid 44.

The far-infrared sensor 11 detects far-infrared radiation emitted from the edge 51 and outputs, to the sensor control section 21, a signal corresponding to the amount of the far-infrared radiation thus detected. Further, the far-infrared sensor 12 detects far-infrared radiation emitted from the edge 52 and outputs, to the sensor control section 21, a signal corresponding to the amount of the far-infrared radiation thus detected. Further, the far-infrared sensor 13 detects far-infrared radiation emitted from the edge 53 and outputs, to the sensor control section 21, a signal corresponding to the amount of the far-infrared radiation thus detected. Further, the far-infrared sensor 14 detects far-infrared radiation emitted from the edge 54 and outputs, to the sensor control section 21, a signal corresponding to the amount of the far-infrared radiation thus detected.

As shown in FIG. 3, the edges 51 and 52 are placed opposite to each other on a transverse axis 61 that is parallel to a horizontal (side-to-side) direction of the eyeball. Meanwhile, the edges 53 and 54 are placed opposite to each other on a longitudinal axis 62 that is parallel to a vertical (up-and-down) direction of the eyeball. As will be described in detail later, the eyeball movement detection device 1 detects, on the basis of a time shift in difference between the output from the far-infrared sensor 11 and the output from the far-infrared sensor 12, a movement of the eyeball in a direction (side-to-side direction) that is parallel to the transverse axis 61. Further, the eyeball movement detection device 1 detects, on the basis of a time shift in difference between the output from the far-infrared sensor 13 and the output from the far-infrared sensor 14, a movement of the eyeball in a direction (up-and-down direction) that is parallel to the longitudinal axis 62.

(Temperature Distribution of Exposed Surface of Eyeball)

Figure 4:
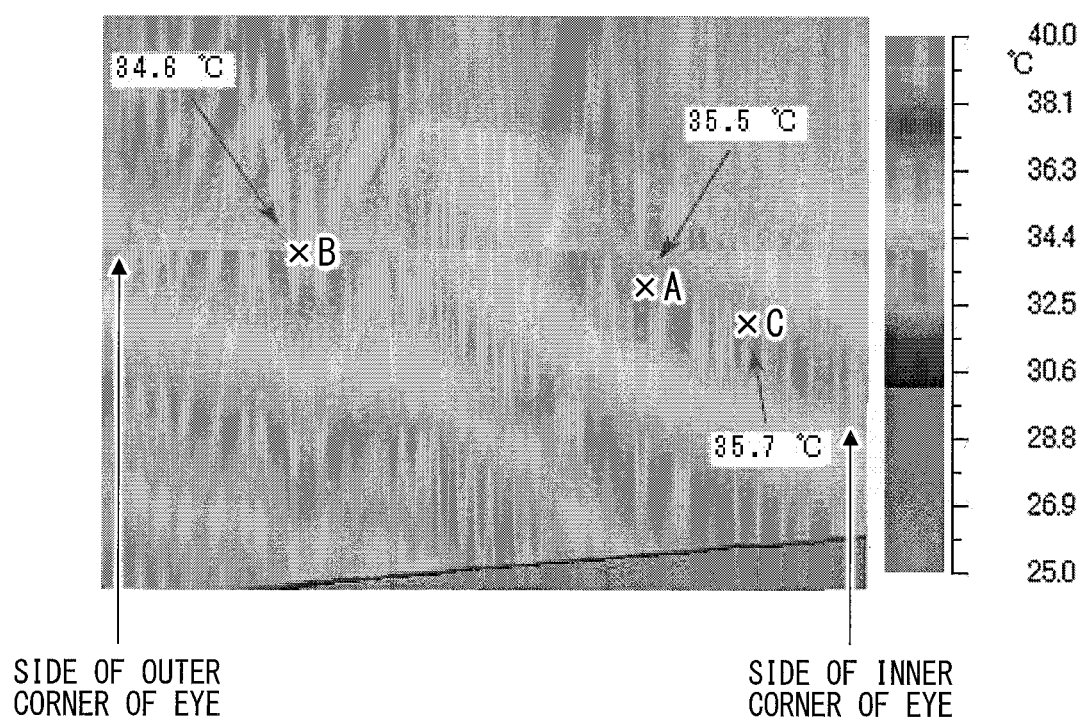
FIG. 4 is a diagram showing an example of a far-infrared thermographic image taken of the right eye of a subject when the subject transferred the subject's line of sight from the front toward the right.

The principle on which the eyeball movement detection device 1 detects an eyeball movement is described below with reference to FIG. 4. FIG. 4 is a diagram showing an example of a far-infrared thermographic image taken of the right eye of a subject when the subject transferred the subject's line of sight from the front toward the right. In FIG. 4, the right side corresponds to the side of the inner corner of the right eye, and the left side corresponds to the side of the outer corner of the right eye. In FIG. 4, the temperatures at points A, B, and C on the exposed surface of the eyeball are 34.6 degrees, 35.5 degrees, and 35.7 degrees, respectively. The points B is on the side of the outer corner of the eye, and the point C is on the side of the inner corner of the eye. Thus, when the subject transfers the subject's line of sight from the front toward the right, temperatures on the exposed surface of the eyeball of the right eye vary from position to position within the surface.

As a result of diligent study of the principle of occurrence of such a temperature distribution of an eyeball as that shown in FIG. 4, the inventor of the present invention clarified that this temperature distribution occurs due to an eyeball movement. Specifically, the inventor found that the principle of this temperature distribution is a transient phenomenon in which a part of the eyeball that is warmed within the orbit loses heat by newly exposed to the air by an eyeball movement. The eyeball movement detection device 1 of the present embodiment detects an eyeball movement on this principle, which is different from the principles on which the conventional methods are based.

(Outputs from Far-Infrared Sensors 11 to 14)

Figure 5:
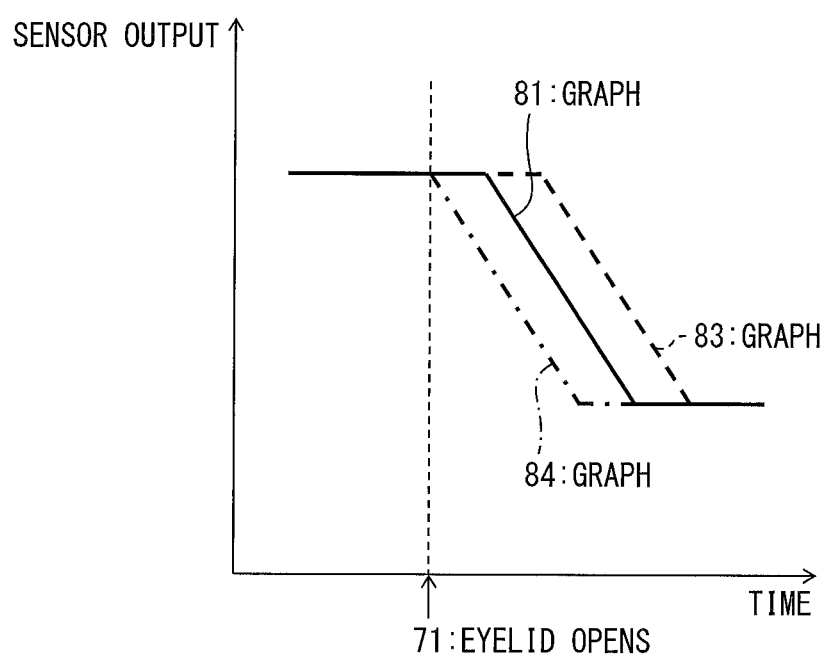
FIG. 5 is a diagram showing examples of time shifts in output from far-infrared sensors as observed when the upper eyelid of the right eye opened in Embodiment 1 of the present invention.

FIG. 5 is a diagram showing examples of time shifts in output from the far-infrared sensors 11 to 14 as observed when the upper eyelid 43 of the right eye changed from a closed state to an open state. In FIG. 5, the longitudinal axis represents the outputs from the far-infrared sensors 11 to 14, and the transverse axis represents time. The point in time 71 represents the moment at which the upper eyelid 43 opened. The graph 81 shows the time shift in output from the far-infrared sensor 11 or 12. The graph 83 shows the time shift in output from the far-infrared sensor 13. The graph 84 shows the time shift in output from the far-infrared sensor 14.

The graphs 81, 83, and 84 take the form of curves under normal conditions, as they show time shifts in temperature of the edges 51 (52), 53, and 54 of the exposed surface 50 of the eyeball. However, in the present embodiment, all of these graphs 81, 83, and 84 are represented by straight lines for convenience of explanation.

While the upper eyelid 43 is closed, the eyeball of the right eye 40 is protected from the outside air. During this period, the eyeball of the right eye 40 is warmed by body temperature, and the lacrimal gland of the right eye 40 secretes tears that then cover the surface of the eyeball. When the upper eyelid 43 opens, a part of the surface of the eyeball becomes exposed. At this point in time, if the temperature of the outside air is lower than the body temperature, the exposed surface 50 of the eyeball loses heat by coming into contact with the outside air. On the other hand, if the temperature of the outside air is higher than the body temperature, the exposed surface 50 of the eyeball loses the heat of vaporization due to drying of the tears covering the exposed surface 50 of the eyeball. In either case, when the upper eyelid 43 opens, the temperature of the entire exposed surface 50 of the eyeball of the right eye 40 gradually decreases with time.

The upper eyelid 43 opens from the lower side toward the upper side of the right eye 40. In this case, the eyeball of the right eye 40 becomes exposed to the outside air from the lower portion upward. Therefore, the edges 51 to 54 decrease in temperature at different timings. Specifically, when the upper eyelid 43 opens, the edge 54, of the edges 51 to 54, becomes exposed to the outside air first, as the edge 54 is on the side of the lower eyelid 44. Next, the edge 51 on the side of the inner corner 41 of the eye and the edge 52 on the side of the outer corner 42 of the eye become exposed to the outside air. At last, after the upper eyelid 43 has completely opened, the edge 53 on the side of the upper eyelid 43 becomes exposed to the outside air. Therefore, after the upper eyelid 43 has opened, it is the edge 54 that starts decreasing in temperature first, the edges 51 and 52 next, and the edge 53 last.

There are also differences in time shift in output from the far-infrared sensors 11 to 14 after the opening of the upper eyelid 43. Specifically, as shown in FIG. 5, after the upper eyelid 43 has opened, the graph 84 of the output from the far-infrared sensor 14, which has directivity to the edge 54 on the side of the lower eyelid 44, rises first (starts decreasing in output). After a certain period of time, the graph 81 of the output from the far-infrared sensor 11, which has directivity to the edge 51 on the side of the inner corner 41 of the eye (or the output from the far-infrared sensor 12, which has directivity to the edge 52 on the side of the outer corner 42 of the eye), rises. After a further certain period of time, the graph 83 of the output from the far-infrared sensor 13, which has directivity to the edge 53 on the side of the upper eyelid 43, rises.

Normally, the time required for the right eye 40 to make a blink ranges from 100 to 150 ms. Intervals between blinks are said to range from approximately 5 to 20 times/min (3 s/time), although there are differences in age and variations among individuals. In comparison with these periods of time, the far-infrared sensors 11 to 14 are sufficiently high in response speed. Specifically, the far-infrared sensors 11 to 14 have a response speed of at lowest approximately 10 ms. Therefore, the eyeball movement detection device 1 can accurately detect a time difference in start among rising edges of the outputs from the far-infrared sensors 11 to 14 after the opening of the upper eyelid 43. As will be described in detail in Embodiment 2, the eyeball movement detection device 1 can accurately detect the occurrence of a blink in the right eye 40 by detecting this time difference.

The present embodiment describes an example in which the eyeball movement detection device 1 detects an eyeball movement of the right eye 40 in a side-to-side direction.

(Time Shift in Output from Far-Infrared Sensors 11 and 12)

Figure 6:
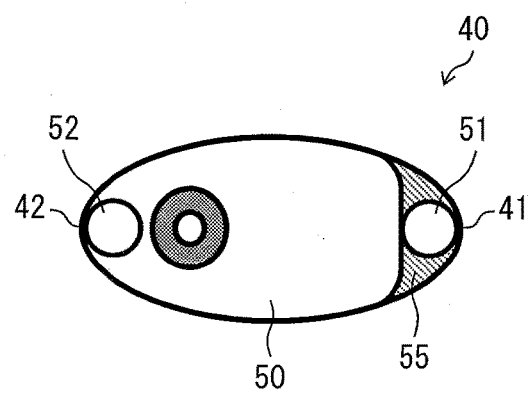
FIG. 6 is a diagram showing the right eye of a user having transferred his/her line of sight toward the right in Embodiment 1 of the present invention.

FIG. 6 is a diagram showing the right eye 40 of the user having transferred his/her line of sight toward the right. As shown in FIG. 6, when the user's line of sight is transferred toward the right (toward the edge 52 on the side of the outer corner 42 of the eye) by an eyeball movement, the edge 52 switches to another portion of the exposed surface 50 that had been exposed before the line of sight was transferred. Meanwhile, the edge 51, located on the side opposite to the edge 52, switches to an exposed part 55 of the surface of the eyeball that had been contained in the orbit before the line of sight was transferred and that is newly exposed from the orbit by the eyeball movement.

Since the eyeball is warmed by the body temperature within the orbit, the temperature of the exposed part 55, which is newly exposed from the orbit by the eyeball movement, is higher than that of the exposed surface 50, which had been exposed before the eyeball movement. Therefore, when an eyeball movement occurs as described above, the temperature of the edge 51 of the exposed surface 50 of the eyeball temporarily becomes higher by the exposed part 55 being newly placed at the edge 51. Meanwhile, nothing of that happens at the edge 52.

Figure 7:
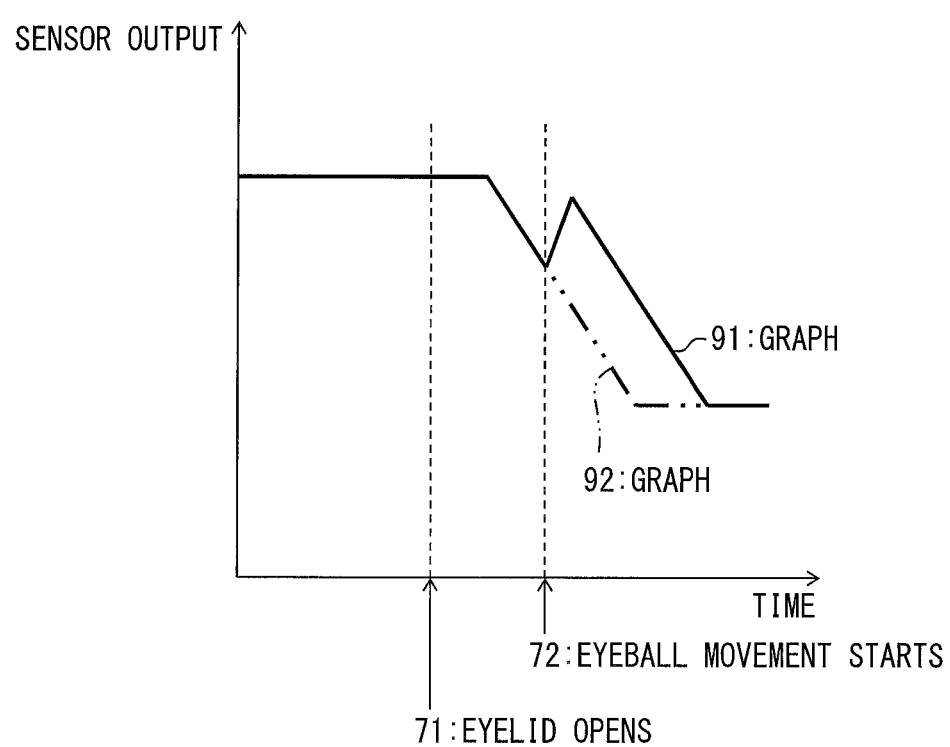
FIG. 7 is a diagram showing an example of a time shift in output from a far-infrared sensor with directivity to an edge on the side of the inner corner of an eye and an example of a time shift in output from a far-infrared sensor with directivity to an edge on the side of the outer corner of the eye as observed when the upper eyelid of the right eye opened and then the user made an eyeball movement in which he/she transferred his/her line of sight toward the right in Embodiment 1 of the present invention.

FIG. 7 is a diagram showing an example of a time shift in output from the far-infrared sensor 11 and an example of a time shift in output from the far-infrared sensor 12 as observed when the upper eyelid 43 of the right eye 40 opened and then the user made an eyeball movement in which he/she transferred his/her line of sight toward the right. In FIG. 7, the longitudinal axis represents the outputs from the far-infrared sensors 11 and 12, and the transverse axis represents time. The point in time 71 represents the moment at which the upper eyelid 43 opened. The point in time 72 represents the moment at which the eyeball movement got started. The graph 91 shows the time shift in output from the far-infrared sensor 11. The graph 92 shows the time shift in output from the far-infrared sensor 12.

As shown in FIG. 7, both of the outputs from the far-infrared sensors 11 and 12 start decreasing a certain period of time after the point in time 71, at which the upper eyelid 43 opened. This is because, as mentioned above, it takes a certain period of time for the edges 51 and 52 to start being exposed to the outside air after the opening of the upper eyelid 43. Since the edges 51 and 52 start being exposed to the outside air at the same time, both of the outputs from the far-infrared sensors 11 and 12 start decreasing at the same timing.

Immediately after the point in time 72, at which the eyeball movement in which the user transfers his/her line of sight toward the right gets started, the output from the far-infrared sensor 11 temporarily increases and then decreases again. Meanwhile, the output from the far-infrared sensor 12 continues decreasing without rising like the output from the far-infrared sensor 11. This is because, as mentioned above, the switching of the edge 51 to the warm exposed part 55 from the orbit immediately after the start of the eyeball movement causes the far-infrared sensor 11 to temporarily receive a larger amount of far-infrared radiation. Since the exposed part 55 gradually decreases in temperature by being exposed to the outside air, the output from the far-infrared sensor 11 temporarily increases but starts decreasing again in the same manner as the output from the far-infrared sensor 12.

In a case where the upper eyelid 43 has been kept open for a sufficiently long period of time, both of the temperatures of the edges 51 and 52 decrease to the same constant temperature at a certain point in time and are kept at the constant temperature afterward. In this case, both of the outputs from the far-infrared sensors 11 and 12 decrease to the same constant value at a certain point in time and are kept at the constant value afterward. Since, as mentioned above, the output from the far-infrared sensor 11 temporarily increases due to the eyeball movement, the decrease in output from the far-infrared sensor 12 ends earlier than the decrease in output from the far-infrared sensor 11.

In the eyeball movement detection device 1, the sensor control section 21 receives an output from the far-infrared sensor 11 and an output from the far-infrared sensor 12 and outputs them to the output difference calculation section 22. The output difference calculation section 22 subtracts an output from the far-infrared sensor 12 from an output from the far-infrared sensor 11 produced at the same point in time as the output from the far-infrared sensor 12 and thereby calculates a difference between the output from the far-infrared sensor 11 and the output from the far-infrared sensor 12. The output difference calculation section 22 calculates such output differences at different points in time and outputs them to the line-of-sight transfer direction detection section 23 and the line-of-sight transfer amount detection section 24 as needed. The line-of-sight transfer direction detection section 23 detects a direction of transfer (rightward direction or leftward direction) of the user's line of sight on the basis of a time shift in the differences thus inputted. Meanwhile, the line-of-sight transfer amount detection section 24 detects an amount of transfer of the user's line of sight on the basis of the time shift in the differences thus inputted.

Figure 8:
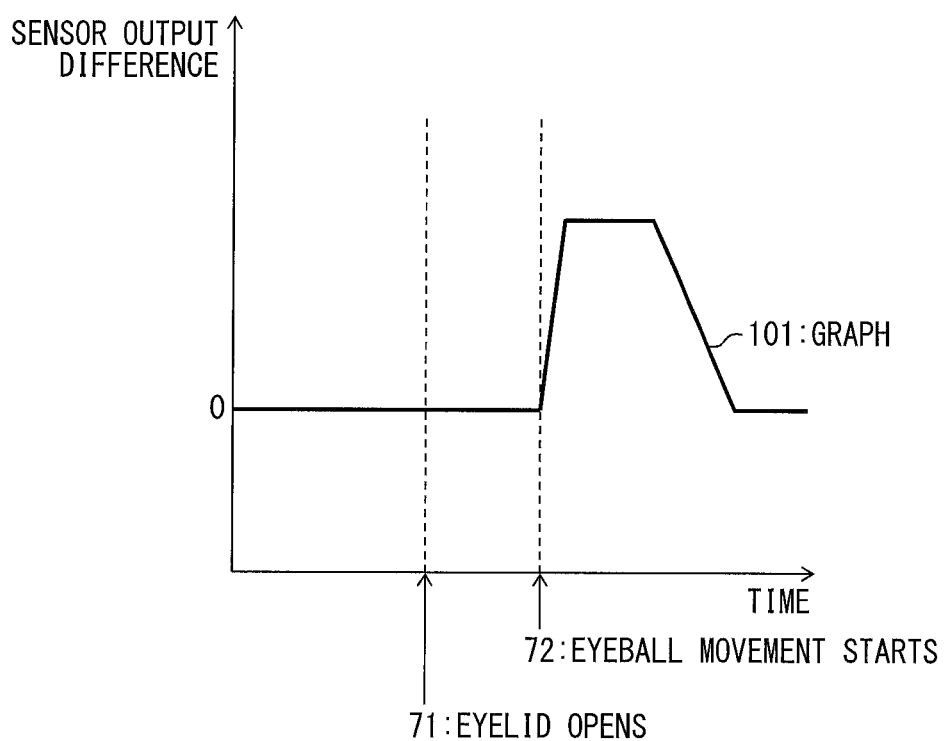
FIG. 8 is a diagram showing an example of a time shift in difference between the output from the far-infrared sensor with directivity to the edge on the side of the inner corner of the eye and the output from the far-infrared sensor with directivity to the edge on the side of the outer corner of the eye as observed when the upper eyelid of the right eye opened and then the user made an eyeball movement in which he/she transferred his/her line of sight toward the right in Embodiment 1 of the present invention.

These methods of detection are described below with reference to FIG. 8. FIG. 8 is a diagram showing an example of a time shift in difference between the output from the far-infrared sensor 11 and the output from the far-infrared sensor 12 as observed when the upper eyelid 43 of the right eye 40 opened and then the user made an eyeball movement in which he/she transferred his/her line of sight toward the right. In FIG. 8, the longitudinal axis represents the output difference obtained by subtracting the output from the far-infrared sensor 12 from the output from the far-infrared sensor 11, and the transverse axis represents time. The graph 101 shows the time shift in output difference.

(Detection of Line-of-Sight Transfer Direction)

As shown by the graph 101 in FIG. 8, the output difference is zero during a period between the point in time 71, at which the upper eyelid 43 opened, and the point in time 72, at which the eyeball movement gets started. This is because the outputs from the far-infrared sensors 11 and 12 shift in the same manner during this period. Meanwhile, after the point in time 72, at which the eyeball movement gets started, the output difference starts rising. This rising edge is directed toward the positive polarity. The output difference rises in this manner because, as mentioned above, the output from the far-infrared sensor 11 temporarily increases after the point in time 72, at which the eyeball movement gets started.

As shown in FIG. 8, at the occurrence of the eyeball movement in which the line of sight is transferred toward the right, the time shift in the output difference obtained by subtracting the output from the far-infrared sensor 12 from the output from the far-infrared sensor 11 rises toward the positive polarity. Accordingly, the line-of-sight transfer direction detection section 23 detects the transfer direction of the eyeball movement on the basis of the direction of a rising edge of the time shift in the output difference inputted from the output difference calculation section 22. Specifically, in a case where the time shift in output difference rises toward the positive polarity, the line-of-sight transfer direction detection section 23 detects a rightward direction as the transfer direction of the eyeball movement.

On the other hand, although not illustrated, at the occurrence of an eyeball movement in which the line of sight is transferred toward the left, the time shift in the output difference obtained by subtracting the output from the far-infrared sensor 12 from the output from the far-infrared sensor 11 rises toward the negative polarity. Accordingly, in a case where the time shift in output difference rises toward the negative polarity, the line-of-sight transfer direction detection section 23 detects a leftward direction as the transfer direction of the eyeball movement.

(Detection of Line-of-Sight Transfer Amount)

The more the user transfers his/her line of sight toward the right, the more range of the edge 51 the exposed part 55 replaces and, therefore, the larger amount of far-infrared radiation the far-infrared sensor 11 receives. Therefore, the more the user transfers his/her line of sight toward the right, the more the output from the far-infrared sensor 11 temporarily increases. This causes the time shift in output difference to rise at a larger angle. That is, the angle of a rising edge of the time shift in output difference is proportional to the amount of transfer of the line of sight. Accordingly, the line-of-sight transfer amount detection section 24 detects the amount of transfer of the line of sight on the basis of the angle of a rising edge of the time shift in the output difference received from the output difference calculation section 22. Specifically, the larger the angle is, the larger transfer amount the line-of-sight transfer amount detection section 24 detects. That is, the line-of-sight transfer amount detection section 24 detects, as the amount of transfer of the line of sight, an amount that is relatively proportional to the angle of the rising edge.

The line-of-sight transfer direction detection section 23 outputs the detected direction of transfer of the line of sight to the communication section 25. The line-of-sight transfer amount detection section 24 outputs the detected amount of transfer of the line of sight to the communication section 25. The communication section 25 notifies the external computer of the inputted direction and amount of transfer of the line of sight as results of detection of the eyeball movement. The external computer executes a process based on the notified direction and amount of transfer of the line of sight. This allows the user to operate the external computer by moving his/her eyes.

Advantages of Present Embodiment

As described above, the eyeball movement detection device 1 detects an eyeball movement of the right eye 40 on the basis of a time shift in difference between an output from the far-infrared sensor 11 and an output from the far-infrared sensor 12. This makes it possible to accurately detect an eyeball movement in which the line of sight is transferred toward the right (i.e. toward the edge 52) or toward the left (i.e. toward the edge 51).

The far-infrared sensors 11 and 12 of the eyeball movement detection device 1 are both noncontact sensors. Furthermore, the eyeball movement detection device 1 does not require image processing for detecting an eyeball movement and can therefore operate with a light weight and with low power consumption. In short, the eyeball movement detection device 1 can detect an eyeball movement in a noncontact manner, with a light weight, and with low power consumption.

Further, the eyeball movement detection device 1 detects the direction of transfer of the line of sight on the basis of the direction of a rising edge of the time shift in the output difference obtained by subtracting the output from the far-infrared sensor 12 from the output from the far-infrared sensor 11. This makes it possible to accurately detect the direction of transfer of the line of sight.

Further, the eyeball movement detection device 1 detects the amount of transfer of the line of sight on the basis of the angle of a rising edge of the time shift in the output difference obtained by subtracting the output from the far-infrared sensor 12 from the output from the far-infrared sensor 11. This makes it possible to accurately detect the amount of transfer of the line of sight.

In a case where the user is a person who does not require visual correction, it is desirable that the spectacles 30 be spectacles for show whose lens-fitting parts are fitted with pieces of glass having no lens function. This allows the lenses to keep the eyeball out of wind, thus making it possible to prevent the temperature of the exposed surface 50 of the eyeball from being changed by the wind and, as a result, to prevent the eyeball movement detection device 1 from malfunctioning.

In the eyewear according to PTL 1 described above, the first and second electrodes are provided on the surfaces of the nose pads. Therefore, this conventional technology has a shortcoming of being unable to be applied to eyewear without nose pads. On the other hand, the eyeball movement detection device 1 of the present embodiment has no one member that needs to be provided on a nose pad of the spectacles 30. This allows the spectacles 30 to include the eyeball movement detection device 1 without nose pads.

It is generally said that the field of view of one eye of a human is approximately 60 degrees on the side of the inner corner of the eye and the side of the upper eyelid, approximately 70 degrees on the side of the lower eyelid, and approximately 90 to 100 degrees on the side of the outer corner of the eye. That is, a human can move his/her eyes more widely in a side-to-side direction than in an up-and-down direction. Therefore, in a case of operating a computer on the basis of a result of detection of a uniaxial eyeball movement, the user can easily operate the computer in such a case as in the present embodiment where the eyeball movement detection device 1 detects the direction of transfer of the line of sight in the side-to-side direction of the eye.

Embodiment 2

A second embodiment according to the present invention is described below with reference to FIGS. 9 to 12.

Spectacles 30 and an eyeball movement detection device 1 according to the present embodiment are identical in configuration to those according to Embodiment 1. However, the eyeball movement detection device 1 according to the present embodiment differs in that it detects an eyeball movement of the right eye 40 in an up-and-down direction.

(Time Shift in Output from Far-Infrared Sensors 13 and 14)

Figure 9:
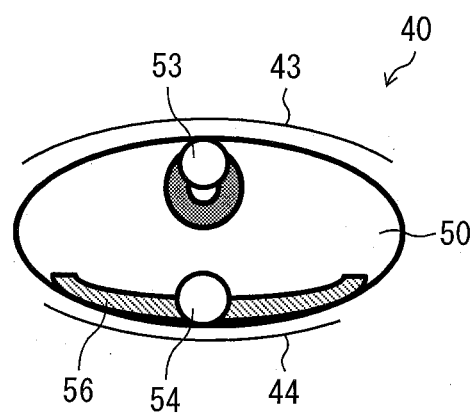
FIG. 9 is a diagram showing the right eye of a user having transferred his/her line of sight upward in Embodiment 2 of the present invention.

FIG. 9 is a diagram showing the right eye 40 of the user having transferred his/her line of sight upward. As shown in FIG. 9, when the user's line of sight is transferred upward (toward the edge 53 of the exposed surface of the eyeball) by an eyeball movement, the edge 53 on the side of the upper eyelid 43 switches to another portion of the exposed surface 50 that had been exposed before the line of sight was transferred. Meanwhile, the edge 54 on the side of lower eyelid 44, located on the side opposite to the edge 53, switches to an exposed part 56 of the surface of the eyeball that had been contained in the orbit before the line of sight was transferred and that is newly exposed from the orbit by the eyeball movement.

The eyeball is warmed by the body temperature within the orbit. Therefore, the temperature of the exposed part 56, which is newly exposed from the orbit by the eyeball movement, is higher than that of the exposed surface 50, which had been exposed before the eyeball movement. Therefore, when an eyeball movement occurs as described above, the temperature of the edge 54 of the exposed surface 50 of the eyeball temporarily becomes higher by the exposed part 56 being newly placed at the edge 54. Meanwhile, nothing of that happens at the edge 53.

FIG. 10 is a diagram showing an example of a time shift in output from the far-infrared sensor 13 and an example of a time shift in output from the far-infrared sensor 14 as observed when the upper eyelid 43 of the right eye 40 opened and then the user made an eyeball movement in which he/she transferred his/her line of sight upward. In FIG. 10, the longitudinal axis represents the outputs from the far-infrared sensors 13 and 14, and the transverse axis represents time. The graph 113 shows the time shift in output from the far-infrared sensor 13. The graph 114 shows the time shift in output from the far-infrared sensor 14.

As mentioned above, when the surface of the eyeball is exposed, the temperature of the surface of the eyeball decreases with time. Because of this, when the upper eyelid 43 opens, the temperature of the edge 54, which becomes exposed first, immediately starts decreasing, whereas the temperature of the edge 53, which is exposed next, starts decreasing in a delayed fashion. For this reason, after the upper eyelid 43 has opened, a rising edge (power reduction) of the output from the far-infrared sensor 14 immediately gets started as indicated by the graph 114. Meanwhile, a rising edge (power reduction) of the output from the far-infrared sensor 13 gets started later than that of the output from the far-infrared sensor 14 as indicated by the graph 113. Since the edges 53 and 54 start being exposed to the outside air at different timings, the outputs from the far-infrared sensors 13 and 14 start decreasing at different timings from each other.

Immediately after the point in time 72, at which the eyeball movement in which the user transfers his/her line of sight upward gets started, the output from the far-infrared sensor 14 temporarily increases and then decreases again. Meanwhile, the output from the far-infrared sensor 13 continues decreasing without rising like the output from the far-infrared sensor 14. This is because, as mentioned above, the switching of the edge 54 to the warm exposed part 56 from the orbit immediately after the start of the eyeball movement causes the far-infrared sensor 14 to temporarily receive a larger amount of far-infrared radiation. Since the exposed part 56 decreases in temperature by being exposed to the outside air, the output from the far-infrared sensor 14 temporarily increases but starts decreasing again in the same manner as the output from the far-infrared sensor 13.

In a case where the upper eyelid 43 has been kept open for a sufficiently long period of time, both of the temperatures of the edges 53 and 54 decrease to the same constant temperature at a certain point in time but are kept at the constant temperature afterward. In this case, both of the outputs from the far-infrared sensors 13 and 14 decrease to the same constant value at a certain point in time and are kept at the constant value afterward. Since, as mentioned above, the output from the far-infrared sensor 14 temporarily increases due to the eyeball movement, the decrease in output from the far-infrared sensor 13 ends earlier than the decrease in output from the far-infrared sensor 14.

In the eyeball movement detection device 1, the sensor control section 21 receives an output from the far-infrared sensor 13 and an output from the far-infrared sensor 14 and outputs them to the output difference calculation section 22. The output difference calculation section 22 subtracts an output from the far-infrared sensor 13 from an output from the far-infrared sensor 14 produced at the same point in time as the output from the far-infrared sensor 13 and thereby calculates a difference between the output from the far-infrared sensor 14 and the output from the far-infrared sensor 14. The output difference calculation section 22 calculates such output differences at different points in time and outputs them to the line-of-sight transfer direction detection section 23 and the line-of-sight transfer amount detection section 24 as needed.

The line-of-sight transfer direction detection section 23 detects a direction of transfer (rightward direction or leftward direction) of the user's line of sight on the basis of a time shift in the differences thus inputted. Meanwhile, the line-of-sight transfer amount detection section 24 detects an amount of transfer of the user's line of sight on the basis of the time shift in the differences thus inputted.

These methods of detection are described below with reference to FIGS. 11 and 12. FIG. 11 is a diagram showing an example of a time shift in difference between the output from the far-infrared sensor 14 and the output from the far-infrared sensor 13 as observed when the upper eyelid 43 opened and then the user made an eyeball movement in which he/she transferred his/her line of sight upward. In FIG. 11, the longitudinal axis represents the output difference obtained by subtracting the output from the far-infrared sensor 13 from the output from the far-infrared sensor 14, and the transverse axis represents time. The graph 121 shows the time shift in output difference.

(Detection of Line-of-Sight Transfer Direction)

As shown by the graph 121 in FIG. 11, the output difference temporarily rises toward the negative polarity after the point in time 71, at which the upper eyelid 43 opened. The output difference continues rising until a point in time 73 at which the output from the far-infrared sensor 13 rises. This is because, as mentioned above, after the upper eyelid 43 has opened, the edge 54 becomes exposed to the outside air first and then, after a certain period of time, the edge 53 becomes exposed to the outside air. There is no change in output from the far-infrared sensor 13, although the output from the far-infrared sensor 14 continues decreasing during a period between the point in time 71, at which the upper eyelid 43 opened, and the point in time 73, at which the output from the far-infrared sensor 13 rises. Therefore, during this period, the output difference shifts toward the negative polarity with time as the output from the far-infrared sensor 14 decreases with time.

Thus, during the period between the point in time 72, at which the upper eyelid 43 opens, and the point in time 73, at which the output from the far-infrared sensor 13 starts rising, the time shift in output difference rises toward the negative polarity even in the absence of an eyeball movement.

During a period between the point in time 73, at which the output from the far-infrared sensor 13 starts rising, and the point in time 72, at which the eyeball movement gets started, both of the outputs from the far-infrared sensors 13 and 14 continue decreasing in the same manner. Therefore, during this period, the output difference maintains a constant value. However, since, as mentioned above, the output from the far-infrared sensor 14 has started decreasing earlier, the output difference is not zero but maintains a constant value of negative polarity during this period.

After the point in time 72, at which the eyeball movement gets started, the output difference starts rising. This rising edge is directed from the negative polarity toward the positive polarity. The output difference rises in this manner because, as mentioned above, the output from the far-infrared sensor 14 temporarily increases after the point in time 72, at which the eyeball movement gets started.

As shown in FIG. 11, the graph 121 includes two rising edges, namely a rising edge produced by the blink and directed toward the negative polarity and a rising edge produced by the eyeball movement and directed from the negative polarity toward the positive polarity. In a case where the line-of-sight transfer direction detection section 23 detects the direction of transfer of the line of sight erroneously on the basis of the former rising edge, the line-of-sight transfer direction detection section 23 detects the direction of transfer of the line of sight erroneously as a downward direction. That is, the eyeball movement detection device 1 malfunctions.

To prevent such malfunction, the eyeball movement detection device 1 according to the present embodiment operates in the following manner. First, the output difference calculation section 22 performs constant monitoring for a time difference between a rising edge of the output from the far-infrared sensor 13 and a rising edge of the output from the far-infrared sensor 13. In the present embodiment, the output from the far-infrared sensor 14 rises first, and then, after a certain period of time, the output from the far-infrared sensor 13 rises. Accordingly, in a case where the output from the far-infrared sensor 13 does not rise at the same time as the output from the far-infrared sensor 14, the output difference calculation section 22 detects the point in time 73, at which the output from the far-infrared sensor 13 rises, as a point in time at which a time difference occurred.

The output difference calculation section 22 discards all outputs received from the far-infrared sensors 13 and 14 before the point in time 73. That is, the output difference calculation section 22 does not calculate an output difference before the point in time 73. Meanwhile, from the point in time 73 forward, the output difference calculation section 22 does not discard outputs received from the far-infrared sensors 13 and 14, calculates an output difference by subtracting the output from the far-infrared sensor 13 from the output from the far-infrared sensor 14, and outputs the output difference to the line-of-sight transfer direction detection section 23 and the line-of-sight transfer amount detection section 24.

FIG. 12 is a diagram showing an example of a time shift in difference between the output from the far-infrared sensor 13 and the output from the far-infrared sensor 14 as observed after detection of a time difference between a rising edge of the output from the far-infrared sensor 13 and a rising edge of the output from the far-infrared sensor 14. In FIG. 12, the longitudinal axis represents the output difference obtained by subtracting the output from the far-infrared sensor 13 from the output from the far-infrared sensor 14, and the transverse axis represents time. The graph 131 shows the time shift in output difference.

As shown in FIG. 12, at the occurrence of the eyeball movement in which the line of sight is transferred upward, the time shift in the output difference obtained by subtracting the output from the far-infrared sensor 13 from the output from the far-infrared sensor 14 rises from the negative polarity toward the positive polarity after the point in time 73. Accordingly, the line-of-sight transfer direction detection section 23 detects the transfer direction of the eyeball movement on the basis of the direction of a rising edge of the time shift in the output difference inputted from the output difference calculation section 22 after the point in time 73. Specifically, in a case where the time shift in output difference rises toward the positive polarity, the line-of-sight transfer direction detection section 23 detects an upward direction as the transfer direction of the eyeball movement.

On the other hand, although not illustrated, at the occurrence of an eyeball movement in which the line of sight is transferred downward, the time shift in output difference rises toward the negative polarity after the point in time 73. Accordingly, in a case where the time shift in output difference rises toward the negative polarity after the point in time 73, the line-of-sight transfer direction detection section 23 detects a downward direction as the transfer direction of the eyeball movement.

(Detection of Line-of-Sight Transfer Amount)

The line-of-sight transfer amount detection section 24 detects the amount of transfer of the line of sight on the basis of the angle of a rising edge of the time shift in the output difference received at or after the point in time 73. That is, line-of-sight transfer amount detection section 24 detects the amount of transfer of the line of sight on the basis of the angle of the rising edge of the graph 131 shown in FIG. 12.

The more the user transfers his/her line of sight upward, the more range of the edge 54 the exposed part 56 replaces and, therefore, the larger amount of far-infrared radiation the far-infrared sensor 14 receives. Therefore, the more the user transfers his/her line of sight upward, the more the output from the far-infrared sensor 14 temporarily increases. This causes the time shift in output difference to rise at a larger angle. That is, the angle of a rising edge of the time shift in output difference at or after the point in time 73 is proportional to the amount of transfer of the line of sight. Accordingly, the line-of-sight transfer amount detection section 24 detects the amount of transfer of the line of sight on the basis of the angle of a rising edge of the time shift in the output difference received from the output difference calculation section 22. Specifically, the larger the angle is, the larger transfer amount the line-of-sight transfer amount detection section 24 detects. That is, the line-of-sight transfer amount detection section 24 detects, as the amount of transfer of the line of sight, an amount that is relatively proportional to the angle of the rising edge.

Advantages of Present Embodiment

As described above, the eyeball movement detection device 1 detects an eyeball movement of the right eye 40 on the basis of a time shift in difference between an output from the far-infrared sensor 14 and an output from the far-infrared sensor 13. This makes it possible to accurately detect an eyeball movement in which the line of sight is transferred upward (i.e. toward the edge 53) or downward (i.e. toward the edge 54).

The far-infrared sensors 13 and 14 of the eyeball movement detection device 1 are both noncontact sensors. Furthermore, the eyeball movement detection device 1 does not require image processing for detecting an eyeball movement and can therefore operate with a light weight and with low power consumption. In short, the eyeball movement detection device 1 can detect an eyeball movement in a noncontact manner, with a light weight, and with low power consumption.

Further, in a case where the output from the far-infrared sensor 13 starts rising after the output from the far-infrared sensor 14 has started rising, the eyeball movement detection device 1 detects the direction of the line of sight on the basis of the time shift in output difference after the point in time 73, at which the output from the far-infrared sensor 13 started rising. This makes it possible to prevent malfunction.

Further, in a case where the output from the far-infrared sensor 13 starts rising after the output from the far-infrared sensor 14 has started rising, the eyeball movement detection device 1 detects the amount of the line of sight on the basis of the time shift in output difference after the point in time 73, at which the output from the far-infrared sensor 13 started rising. This makes it possible to prevent malfunction.

Embodiment 3

A third embodiment according to the present invention is described below.

In the first and second embodiments 1 described above, the eyeball movement detection device 1 includes the four far-infrared sensors 11 to 14 in order to detect both side-to-side and up-and-down directions of an eyeball. On the other hand, in the present embodiment, the eyeball movement detection device 1 includes the far-infrared sensors 11 and 12 of the four far-infrared sensors 11 to 14 and is thereby configured to be able to detect only a movement of an eyeball in a side-to-side direction. Alternatively, the eyeball movement detection device 1 includes the far-infrared sensors 13 and 14 of the four far-infrared sensors 11 to 14 and is thereby configured to be able to detect only a movement of an eyeball in an up-and-down direction.

[Examples of Implementation by Software]

The functional blocks of the eyeball movement detection device 1 shown in FIG. 1 may be implemented by logic circuits (hardware) formed on integrated circuits (IC chips) or the like, or may be implemented by software through the use of a CPU (central processing unit).

In the latter case, the eyeball movement detection device 1 includes a CPU that executes commands in programs serving as software by which the functions are implemented, a ROM (read-only memory) or storage device (both referred to as "storage medium") in which the programs and various types of data are computer-readably stored, a RAM (random-access memory) to which the programs are loaded, and the like. The object of the present invention is attained by a computer (or a CPU) reading the programs from the storage medium. Usable examples of the storage medium include "non-transient tangible media" such as tapes, disks, cards, semiconductor memories, programmable logic circuits, and the like. Further, the programs may be supplied to the computer via a given transmission medium (such as a communication network or a broadcast wave) via which the programs can be transmitted. It should be noted that the present invention may be implemented in the form of a data signal, embedded in a carrier wave, in which the programs are embodied by electronic transmission.

Modifications

The first to third embodiments described above can be modified, for example, as follows.

The four far-infrared sensors 11 to 14 do not necessarily need to be separate sensors that are independent of one another. For example, the far-infrared sensors 11 to 14 may be an array sensor constituted by a single chip having a plurality of separate light-receiving parts that are independent of one another. In this configuration, each of the light-receiving parts has directivity only to any of the edges 51 to 54.

The eyeball movement detection device 1 can be incorporated into a head mount display device or a spectacle display device, as well as the spectacles 30. Such a mount display device or spectacle display device into which the eyeball movement detection device 1 is incorporated is also encompassed in an embodiment of the present invention. In such a mount display device or spectacle display device, the display serves as a wind shield.

Not all the constituent elements of the eyeball movement detection device 1 need to be provided in the spectacles 30. For example, only the far-infrared sensors 11 to 14 may be provided in the spectacles 30, and the control section 20 may be provided in the external computer, which is an operational object. Such an operating system constituted by the spectacles 30 including the far-infrared sensors 11 to 14 and the external computer including the control section 20 is also encompassed in an embodiment of the present invention.

In the operating system, the far-infrared sensors 11 to 14 and the control section 20 provided in the external computer are connected to each other either wirelessly or by cable. In the case of cable connection, the far-infrared sensors 11 to 14 are connected to the control section 20, for example, via flexible substrates or wires. Outputs from the far-infrared sensors 11 to 14 are sent as needed to the control section 20 provided in the external computer. This modification is the same as the embodiments described above in that the sensor control section 21 detects an eyeball movement of the user on the basis of the outputs from the far-infrared sensors 11 to 14 and the external computer executes a process based on the eyeball movement thus detected.

The temperature of the exposed surface 50 of the eyeball may greatly change under the influence of air temperature or humidity. Given these circumstances, the eyeball movement detection device 1 may include an air temperature sensor or a humidity sensor to correct the detected direction or amount of transfer of the line of sight on the basis of an output from the sensor. This makes it possible to improve the accuracy of the direction and amount of transfer of directivity.

Alternatively, the eyeball movement detection device 1 may take measures to prevent malfunction on the basis of an output from the air temperature sensor or the humidity sensor. For example, in a case where the eyeball movement detection device 1 has detected a rapid change in ambient temperature on the basis of an output from the air temperature sensor, it is preferable that the eyeball movement detection device 1 not notify the external computer of a result of detection of an eyeball movement (i.e. a result of detection of the direction and amount of transfer of the line of sight). This makes it possible to prevent the external computer from being erroneously operated even if the eyeball movement detection device 1 erroneously detects, as an eyeball movement, a rapid change in temperature of the exposed surface 50 of the eyeball caused by a rapid change in ambient temperature.

Further, in a case where the eyeball movement detection device 1 has detected a discomfort index of over 80 on the basis of an output from the air temperature sensor and an output from the humidity sensor, it is preferable that the eyeball movement detection device 1 not notify the external computer of a result of detection of an eyeball movement (i.e. a result of detection of the direction and amount of transfer of the line of sight). This makes it possible to prevent the external computer from being erroneously operated even if the user sweats at a discomfort index of 80 to 85 and the eyeball movement detection device 1 erroneously detects, as an eyeball movement, a rapid change in temperature of the exposed surface 50 of the eyeball caused by the sweat entering the right eye 40.

CONCLUSION

An eyeball movement detection device according to Aspect 1 of the present invention includes:

a first far-infrared sensor (far-infrared sensor 11, far-infrared sensor 13) having directivity to a first edge (edge 51, edge 53) of an exposed surface of an eyeball of an eye of a user;

a second far-infrared sensor (far-infrared sensor 12, far-infrared sensor 14) having directivity to a second edge (edge 52, edge 54) of the exposed surface of the eyeball, the second edge being opposed to the first edge;

a first output difference calculation section (output difference calculation section 22) that calculates a difference between an output from the first far-infrared sensor and an output from the second far-infrared sensor; and a first detection section (line-of-sight transfer direction detection section 23, line-of-sight transfer amount detection section 24) that detects an eyeball movement of the eyeball on the basis of a time shift in the difference thus calculated.

When the user's line of sight is transferred toward the first edge of the exposed surface of the eyeball by an eyeball movement, the first edge switches to another portion of the exposed surface that had been exposed before the line of sight was transferred. Meanwhile, the second edge, located on the side opposite to the first edge, switches to an exposed part of the surface of the eyeball that had been contained in the orbit before the line of sight was transferred and that is newly exposed from the orbit by the eyeball movement.

Since the eyeball is warmed by the body temperature within the orbit, the temperature of the buried surface of the eyeball in the orbit is higher than that of the exposed surface of the eyeball. Therefore, when an eyeball movement occurs as described above, the temperature of the second edge of the exposed surface of the eyeball temporarily becomes higher at the occurrence of an eyeball movement. Meanwhile, nothing of that happens at the first edge.

As a result of this, at the occurrence of an eyeball movement in which the line of sight is transferred toward the first edge, the output from the second far-infrared sensor, which has directivity to the second edge, temporarily increases, but the output from the first far-infrared sensor, which has directivity to the first edge, does not do so. Therefore, the difference between the output from the first far-infrared sensor and the second far-infrared sensor shifts temporally differently according to the extent of eyeball movement.

On the contrary, at the occurrence of an eyeball movement in which the line of sight is transferred toward the second edge, the output from the first far-infrared sensor temporarily increases, but the output from the second far-infrared sensor does not do so. Therefore, in this case, too, the difference between the output from the first far-infrared sensor and the second far-infrared sensor shifts temporally differently according to the extent of eyeball movement.

Note here that, according to the foregoing configuration, the eyeball movement detection device detects an eyeball movement of an eyeball on the basis of a time shift in difference between an output from the first far-infrared sensor and an output from the second far-infrared sensor. This makes it possible to accurately detect an eyeball movement in which the line of sight is transferred toward the first edge or the second edge.

Further, the first and second far-infrared sensors of the eyeball movement detection device according to the present aspect are both noncontact sensors. Furthermore, the eyeball movement detection device according to the present aspect does not require image processing for detecting an eyeball movement and can therefore operate with a light weight and with low power consumption.

Thus, the eyeball movement detection device according to the present aspect can detect an eyeball movement in a noncontact manner, with a light weight, and with low power consumption.

In Aspect 1, an eyeball movement detection device according to Aspect 2 of the present invention is configured such that the first detection section detects a direction of transfer of the user's line of sight on the basis of a direction of a rising edge of the time shift in the difference.

This configuration makes it possible to accurately detect the direction of transfer of the line of sight at the occurrence of an eyeball movement.

In Aspect 1 or 2, an eyeball movement detection device according to Aspect 3 of the present invention is configured such that the first detection section detects an amount of transfer of the user's line of sight on the basis of an angle of a rising edge of the time shift in the difference.

This configuration makes it possible to accurately detect the amount of transfer of the line of sight at the occurrence of an eyeball movement.

In any of Aspects 1 to 3, an eyeball movement detection device according to Aspect 4 of the present invention is configured such that the first far-infrared sensor has directivity to the first edge of the exposed surface of the eyeball on a side of an inner corner of the eye, and the second far-infrared sensor has directivity to the second edge of the exposed surface of the eyeball on a side of an outer corner of the eye.

This configuration makes it possible to accurately detect an eyeball movement of the eye in a transverse direction.

In any of Aspects 1 to 3, an eyeball movement detection device according to Aspect 5 of the present invention is configured such that the first far-infrared sensor has directivity to the first edge of the exposed surface of the eyeball on a side of an upper eyelid, and the second far-infrared sensor has directivity to the second edge of the exposed surface of the eyeball on a side of a lower eyelid.

This configuration makes it possible to accurately detect an eyeball movement of the eye in a longitudinal direction.

In Aspect 5, an eyeball movement detection device according to Aspect 6 of the present invention is configured such that in a case where the output from the first far-infrared sensor starts rising after the output from the second far-infrared sensor has started rising, the first detection section detects the eyeball movement on the basis of the time shift in the difference after a point in time at which the output from the first far-infrared sensor started rising.

In a case where the output from the first far-infrared sensor starts rising after the output from the second far-infrared sensor has started rising, the first detection section detects the eyeball movement on the basis of the time shift in the difference after a point in time at which the output from the first far-infrared sensor started rising.

When the surface of the eyeball is exposed, the temperature of the surface of the eyeball decreases with time. Because of this, when the eye opens, the temperature of the second edge, which becomes exposed first, immediately starts decreasing, whereas the temperature of the first edge, which is exposed next, starts decreasing in a delayed fashion. For this reason, after the eye has opened, a rising edge of the output from the second far-infrared sensor immediately gets started, but a rising edge of the output from the first far-infrared sensor gets started later than that of the output from the second far-infrared sensor.

Thus, during a period between the opening of the eye and the start of a rising edge of the output from the second far-infrared sensor, the time shift in output from the first far-infrared sensor differs from the time shift in output from the second far-infrared sensor even in the absence of an eyeball movement. Therefore, during this period of time, the difference between the output from the first far-infrared sensor and the output from the second far-infrared sensor temporally shifts as if an eyeball movement occurred. This causes an eyeball movement to be erroneously detected on the basis of the time shift in output difference during this period of time.

To address this problem, in a case where the output from the first far-infrared sensor starts rising after the output from the second far-infrared sensor has started rising, the eyeball movement detection device according to the present aspect detects an eyeball movement on the basis of the time shift in the difference after a point in time at which the output from the first far-infrared sensor started rising. In other words, the output difference between the sensors prior to the point in time at which the output from the first far-infrared sensor started rising is ignored. This makes it possible to prevent the occurrence of a blink from being erroneously detected as an eyeball movement.

In any of Aspects 1 to 3, an eyeball movement detection device according to Aspect 7 of the present invention includes:

a third far-infrared sensor (far-infrared sensor 13) having directivity to a third edge (edge 53) of the exposed surface of the eyeball on a side of an upper eyelid;

a fourth far-infrared sensor (far-infrared sensor 14) having directivity to a fourth edge (edge 54) of the exposed surface of the eyeball on a side of a lower eyelid;

a second output difference calculation section (line-of-sight transfer direction detection section 23, line-of-sight transfer amount detection section 24) that calculates a difference between an output from the third far-infrared sensor and an output from the fourth far-infrared sensor; and a second detection section that detects an eyeball movement of the eyeball on the basis of a time shift in the difference calculated by the second output difference calculation section.

This configuration makes it possible to accurately detect both an eyeball movement of the eye in a side-to-side direction and an eyeball movement of the eye in an up-and-down direction.

An eyeball movement detection method according to Aspect 8 of the present invention includes:

an output difference detecting step of calculating a difference between an output from a first far-infrared sensor having directivity to a first edge of an exposed surface of an eyeball of an eye of a user and an output from a second far-infrared sensor having directivity to a second edge of the exposed surface of the eyeball, the second edge being opposed to the first edge; and a detecting step of detecting an eyeball movement of the eyeball on the basis of a time shift in the difference thus calculated.

This configuration makes it possible to detect an eyeball movement in a noncontact manner, with a light weight, and with low power consumption.

Spectacles according to Aspect 9 of the present invention includes an eyeball movement detection device according to any of Aspects 1 to 7.

This configuration makes it possible to provide spectacles that detect an eyeball movement in a noncontact manner, with alight weight, and with low power consumption.

A head mount display device according to Aspect 10 of the present invention includes an eyeball movement detection device according to any of Aspects 1 to 7.

This configuration makes it possible to provide a head mount display device that detects an eyeball movement in a noncontact manner, with a light weight, and with low power consumption.

A spectacle display device according to Aspect 11 of the present invention includes an eyeball movement detection device according to any of Aspects 1 to 7.

This configuration makes it possible to provide a spectacle display device that detects an eyeball movement in a noncontact manner, with a light weight, and with low power consumption.

The eyeball movement detection device described above may be implemented by a computer. In this case, a program that causes a computer to function as the components of the eyeball movement detection device and thereby causes the eyeball movement detection device to be implemented by the computer and a computer-readable storage medium storing the program are also encompassed in the scope pf the present invention.

The present invention is not limited to the description of the embodiments above, but may be altered within the scope of the claims. An embodiment based on a proper combination of technical means disclosed in different embodiments is encompassed in the technical scope of the present invention. Furthermore, a new technical feature may be formed by combining technical means disclosed in each separate embodiment.

INDUSTRIAL APPLICABILITY

The present invention is widely applicable as a device for detecting an eyeball movement.

REFERENCE SIGNS LIST

1 Eyeball movement detection device
11 Far-infrared sensor (first far-infrared sensor)
12 Far-infrared sensor (second far-infrared sensor)
13 Far-infrared sensor (first far-infrared sensor, third far-infrared sensor)
14 Far-infrared sensor (second far-infrared sensor, fourth far-infrared sensor)
20 Control section
21 Sensor control section
22 Output difference calculation section (first output difference calculation section, second output difference calculation section)
23 Line-of-sight transfer direction detection section (first detection section, second detection section)
24 Line-of-sight transfer amount detection section (first detection section, second detection section)
25 Communication section
30 Spectacles
31 Frame

The invention claimed is:

1. An eyeball movement detection device comprising:
   a first far-infrared sensor having directivity to a first edge of an exposed surface of an eyeball of an eye of a user;
   a second far-infrared sensor having directivity to a second edge of the exposed surface of the eyeball, the second edge being opposed to the first edge;
   a first output difference calculation section that calculates a difference between an output from the first far-infrared sensor and an output from the second far-infrared sensor; and
   a detection section that detects an eyeball movement of the eyeball on the basis of a time shift in the difference thus calculated.

2. The eyeball movement detection device according to claim 1, wherein the detection section detects a direction of transfer of the user's line of sight on the basis of a direction of a rising edge of the time shift in the difference.

3. The eyeball movement detection device according to claim 1, wherein the detection section detects an amount of transfer of the user's line of sight on the basis of an angle of a rising edge of the time shift in the difference.

4. The eyeball movement detection device according to claim 1, wherein the first far-infrared sensor has directivity to the first edge of the exposed surface of the eyeball on a side of an inner corner of the eye, and
   the second far-infrared sensor has directivity to the second edge of the exposed surface of the eyeball on a side of an outer corner of the eye.

5. The eyeball movement detection device according to claim 1, wherein the first far-infrared sensor has directivity to the first edge of the exposed surface of the eyeball on a side of an upper eyelid, and
   the second far-infrared sensor has directivity to the second edge of the exposed surface of the eyeball on a side of a lower eyelid.

* * * * *